United States Patent [19]

Richardson

[11] Patent Number: 5,507,722
[45] Date of Patent: Apr. 16, 1996

[54] AMPUTATION CYLINDER DRESSING

[76] Inventor: James V. Richardson, 339 St. Luke's Dr., Montgomery, Ala. 36117

[21] Appl. No.: 354,898

[22] Filed: Dec. 9, 1994

[51] Int. Cl.$^6$ ..................................................... A61F 2/80
[52] U.S. Cl. ............................. 602/62; 602/60; 602/61; 602/63; 623/33; 623/35; 623/36
[58] Field of Search ..................... 602/61, 62, 63, 602/73, 60; 623/33, 34, 35, 36, 37, 16, 57, 58, 59

[56] References Cited

U.S. PATENT DOCUMENTS

| | | | |
|---|---|---|---|
| 3,186,006 | 1/1965 | Miller | 623/36 |
| 3,812,650 | 5/1974 | Dabney | 623/33 X |
| 3,983,870 | 10/1976 | Herbert et al. | 602/63 |
| 4,635,626 | 1/1987 | Lerman | 602/61 |
| 4,872,879 | 10/1989 | Shamp | 623/36 |
| 4,988,360 | 1/1991 | Shamp | 623/36 X |
| 5,108,455 | 4/1992 | Telikicherla | 623/33 |
| 5,314,496 | 5/1994 | Harris et al. | 623/36 X |

*Primary Examiner*—Richard J. Apley
*Assistant Examiner*—Kim M. Lee
*Attorney, Agent, or Firm*—Edmund M. Jaskiewicz

[57] ABSTRACT

A flexible removable dressing for immediate post-operative application around a patient's amputation stump comprises a flexible cylindrical member enclosing a patient's amputation stump and a semi-rigid cup portion detachably connected to the bottom end of the cylindrical portion to fit upon the bottom portion of the amputation stump. Padding of a soft resilient material is positioned within the cup portion. The diameter of the cylindrical portion is adjustable in size.

6 Claims, 3 Drawing Sheets

AMPUTATION CYLINDER DRESSING

The present invention relates to a removable flexible dressing for immediate postoperative application around a patient's amputation stump, more particularly, such a dressing having a cylindrical portion encircling the limb above the amputation stump and a detachable cup portion positioned on the bottom of the amputation stump.

Following a leg amputation, it is necessary to provide a dressing to protect the amputation stump. Such a dressing should not only completely and securely enclose the amputation stump but should be readily removable for frequent and periodic medical examination of the stump itself. At the same time, the dressing should be of such a nature as to be readily applied after the operation with a minimum of effort and preferably by medical personnel who are not required to have a vast or comprehensive knowledge of the dressing of amputations and the application of dressings to such amputation stumps.

One previous procedure for dressing of the amputation stump consisted of applying dressings and specialized bandages, to the stump and it was necessary that a surgeon or someone particularly skilled in such dressings apply the bandages. It is obvious that since an expert was required to apply the bandages, likewise, an expert also was required to remove the bandage for examination of the stump.

Various forms of appliances and devices have been proposed for the shrinking or reducing the cross sectional size of an amputation stump. An example of one such device is U.S. Pat. No. 4,644,946 to Cremona-Bonato. However, these appliances are all constructed to apply uniform compressive pressure against the amputation stump and, for this purpose, are provided with various structural features apply these forces. It is readily apparent that such devices are more complicated in structure than would be a dressing intended for immediate post-operative use.

It is therefore the principal object of the present invention to provide a novel and improved removable dressing for post operative application around a patient's amputation stump.

It is an additional object of the present invention to provide such a flexible dressing which can be readily adjusted to different sizes while at the same time providing a secure positioning of the bandage to the amputation stump.

It is another object of the present invention to provide such a dressing which can be readily applied and removed by relatively untrained personnel.

It is a further object of the present invention to provide such a dressing which is simple in construction and inexpensive to manufacture such that the dressing is readily disposable without incurring excessive expense.

It is still another object of the present invention to provide such a dressing which is comfortable to wear yet will remain in position on the patient without the need for frequent adjustment.

The objects of the present invention are achieved and the disadvantages of the prior art are overcome by the removable flexible dressing disclosed herein which essentially comprises a flexible, cylindrical portion having an open end top and a bottom end and shaped to enclose and secure a patient's amputation stump. A semi-rigid cup portion is at the bottom end of the cylindrical portion and is shaped to fit upon the bottom portion of the amputation stump. The cup portion is detachably connected to the cylindrical portion. Means are also provided for adjusting the diameter of the cylinder portion and a soft resilient pad is preferably provided in the cup portion to bear against the bottom end of the amputation stump.

The dressing according to the present invention may be employed both in above and below the knee amputations. Slight modifications are provided depending on the particular location and these modifications will be discussed in detail below.

Other objects and advantages of the present invention will be apparent upon reference to the accompanying description when taken in conjunction with the following drawings, which are exemplary, wherein.

Proceeding next to the drawings wherein like reference symbols indicate the same parts throughout the various views a specific embodiment and modifications of the present invention will be described in detail.

Figure 1:
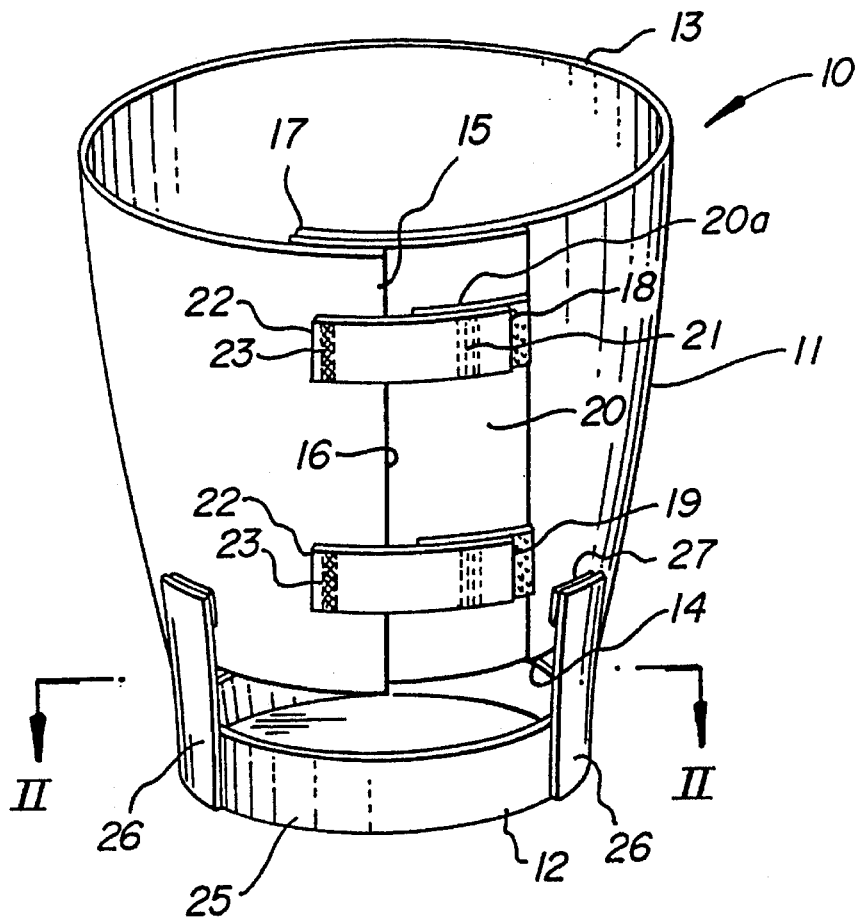
FIG. 1 is a top perspective view of the removable flexible dressing according to the present invention.

The flexible dressing of the present invention is indicated generally at 10 in FIG. 1 and comprises a flexible cylindrical portion 11 and a semi-rigid cup portion 12. The cylindrical portion 11 has a top end 13 and a bottom end 14 and has an axial opening or cut 15 extending between the top and bottom ends. The axial opening 15 thus defines axial edges 16 and 17. The cylindrical portion 11 is preferably formed from a flexible heavy duty woven cloth similar to canvas and known as "ducking".

Both the upper and lower ends 13 and 14 are open such that the cylindrical portion 11 is tubular in shape.

The cylindrical portion 11 is adjustable such that the diameter may be varied or the cylindrical shape may be given a somewhat tapering configuration, as illustrated in FIG. 1 to more closely fit upon the patient's limb above the amputation stump.

The cylindrical portion 11 is provided with a detachable self-gripping fastening means 18 and 19 of the VELCRO type. This Velcro type of fastening means is well-known in the art and is readily available commercially. The product comprises complimentary fabric sections which in the present embodiment comprises a nap surface 20 which is secured to the outer surface of the tubular member 11 extending from the axial edge 17 as may be seen in FIG. 1 of the drawings. The fastening means further comprises hook surfaces 20a which are attached to the undersides of the fastening members 18 and 19 and in the present embodiment are attached by the indicated stitching 21. This hook surface comprises a plurality of closely spaced rows of small plastic hooks which tightly grip the nap surface in a manner known in the art and remain gripped until they are released by manually pulling apart the sections in a direction normal to their engaged surfaces.

The fastening members 18 and 19 are also secured at their other ends 22 to the outer surface of the cylindrical portion 11 adjacent the axial edge 16 as shown and are preferably attached by stitching 23 as shown.

Figure 2:
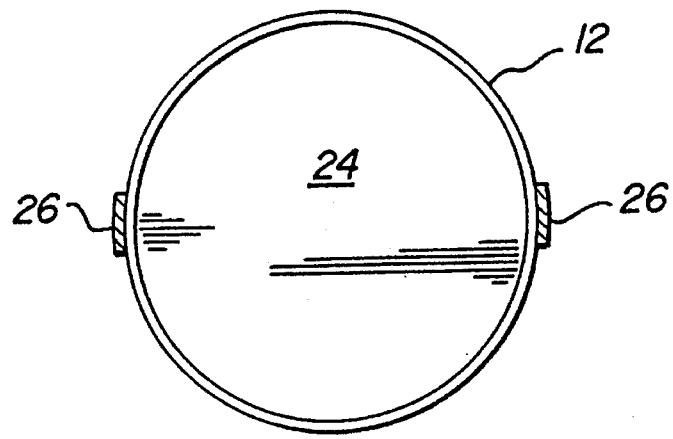
FIG. 2 is a sectional view taken along the line 1—1 of FIG. 1.

The bottom or cup portion 12 comprises a circular bottom member 24 from the peripheral edge of which there is upstanding a cylindrical wall 25. These components 24 and 25 are also made from a flexible ducking material similar to that of a cylindrical portion 11 and are stitched or otherwise permanently secured together at the peripheral edge of the bottom 24. The cup portion 12 is provided with a pair of diametrically opposed detachable connecting members 26 attached to the outer surface of the upstanding wall portion 25 as shown in FIGS. 1 and 2. The connecting members 26 attach in a similar manner as described above and are provided with VELCRO type fastenings wherein a hook portion on the upper inner surfaces of the connecting members 26 connects with nap portions 27 located on the outer bottom surface of the cylindrical portion 11 as shown.

Disposed within the cup portion 12 are soft resilient pads which are intended to bear against the bottom of the amputation stump. These pads may be formed from a plastic foam or "lambs wool" in a manner known in the art. These pads which are indicated at 28 in FIG. 3 may be provided on the bottom surfaces with VELCRO type fastening members so as to be attached to the bottom inside surface of the cup portion 12.

When used as an immediate post-operative dressing, the dressing according to the present invention is readily and easily mounted to the amputation stump by positioning the cylindrical portion thereon and adjusting its diameter and subsequently placing the cup portion against the bottom of the amputation stump and attaching the cup portion by the self-griping fastening means to the outer surface of the cylindrical portion as described above.

Figure 3:
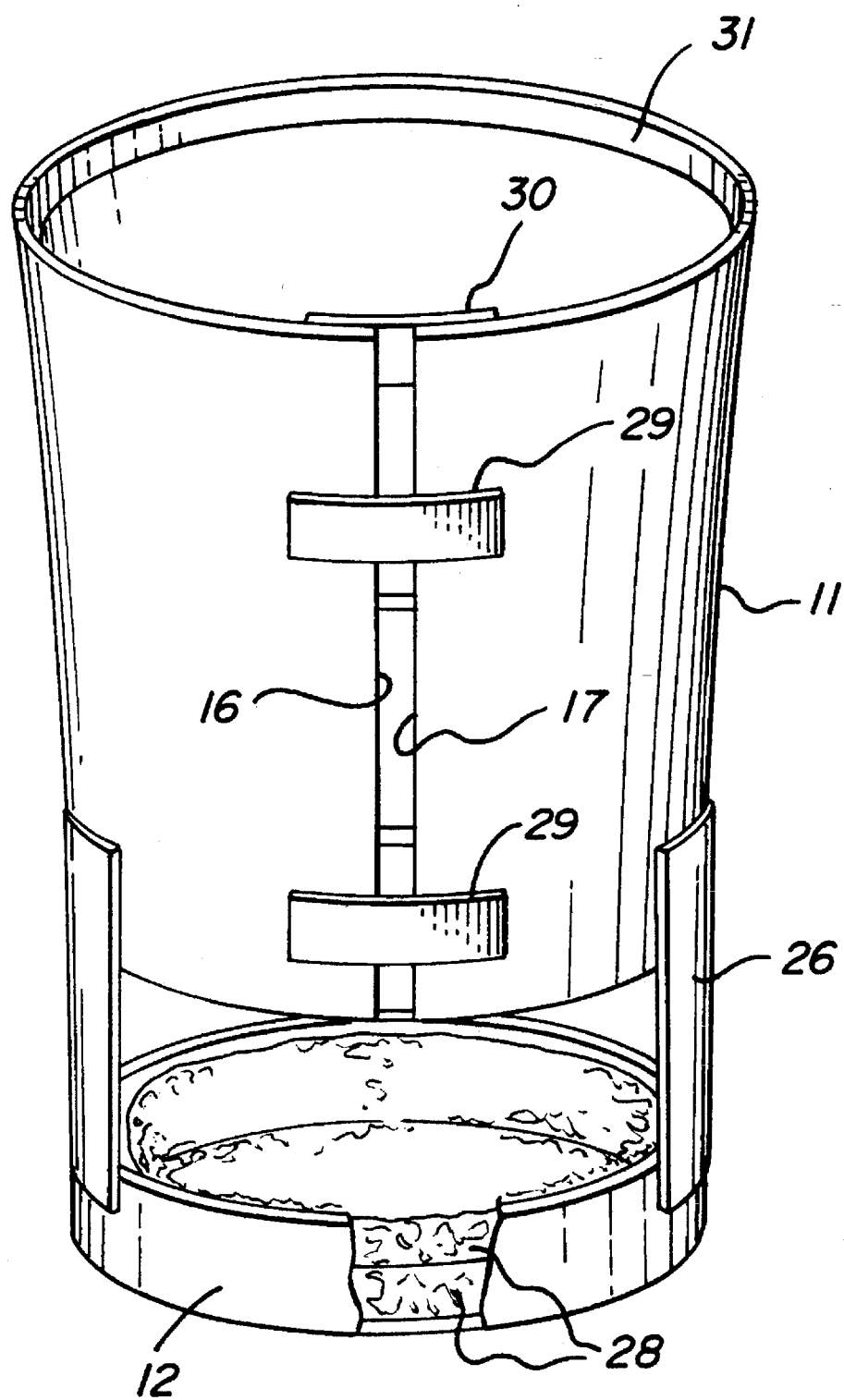
FIG. 3 is a view similar to that of FIG. 1 but showing a modification of the dressing.

In FIG. 3 there is disclosed a modification of the present invention wherein the cylindrical portion 11 is provided with axial edges 16 and 17 which are not intended to overlap but are secured in a spaced position as shown by the detachable self-gripping fasteners 29 as illustrated. As a further fastening element, there is provided an additional self-gripping fastening member 30 on the inner surfaces of the cylindrical portion 11 at the upper edge thereof as shown. There are also provided narrow bands 31 of a fabric non-slip material on the inner surface of the cylindrical portion along the upper edge thereof, along the bottom edge thereof and at the middle of the cylindrical portion to help secure the cylindrical portion in position. This modification is similarly provided with a cup portion 12 secured by self-gripping fasteners 26 as described above.

Figure 4:
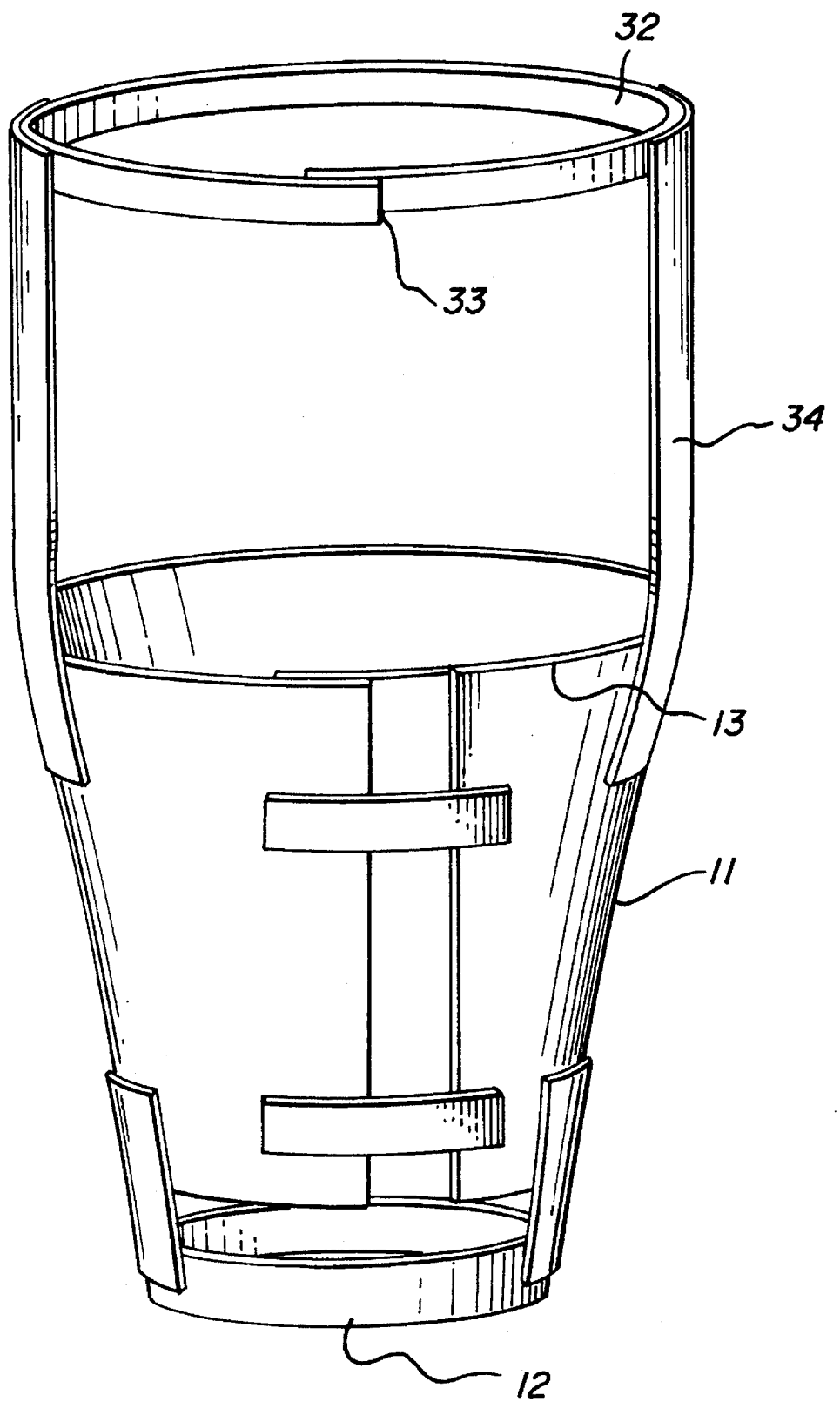
FIG. 4 is a perspective view similar to that of FIGS. 1 and 3 but showing a further modification intended for a below the knee amputation.

In FIG. 4 there is shown a modification of the present invention which is particularly adapted for a below the knee amputation. In this modification there is provided a cylindrical portion 11 and a cup portion 12 as described above but when in use, the cylindrical portion is positioned about the leg below the knee just above the amputation stump. To help secure the dressing in position there is further provided a band 32 of a non-slip fabric material and this band has overlapping ends at 33 which are connected together by a detachable self-gripping fastener of the VELCRO type as described above. A pair or more, if desired, of heavy duty fabric strips 34 connect the band 32 to the upper portion of the cylindrical portion 11 as shown in FIG. 4. This structure permits the space above the top edge 13 of the cylindrical portion and the band 32 to be open to the knee cap of the patient.

While other heavy duty cloth materials could also be used to construct the several components of this invention, the described ducking material is preferred since it is very strong and is much more comfortable to the wearer than would be, for example, a nylon material. Further, as previously described, while VELCRO type materials are preferable for use as the fastening means, it is apparent that other types of fastening arrangements could be used if desired for particular applications, for example, plastic zippers or the like fasteners could be used to interconnect the axial edges of the cylindrical portion as disclosed in FIG. 1 and other forms of quick release or detachable type fasteners could be used to secure the straps 26 to the lower portion of the cylindrical portion 11.

Thus it can be seen that the present invention has disclosed a removable flexible dressing for immediate post-operative application around a patient's amputation stump and can be used as a long term protective device, whether or not a post prosthesis is used or not. The dressing is simple in construction, reliable in use and can be readily applied and removed by relatively unskilled personnel. While primarily intended as an early post operative device for protection of the amputation stump, the dressing can be used as a long term protective device when post prosthesis is not in use or for some medical reason cannot or will not be used.

It will be understood that this invention is susceptible to modification in order to adapt it to different usages and conditions, and accordingly, it is desired to comprehend such modifications within this invention as may fall within the scope of the appended claims.

What is claimed is:

1. A removable, flexible, post-operative amputation stump dressing for immediate post-operative application around a patient's amputation stump, said amputation stump having a bottom portion, said dressing comprising:

a flexible cylindrical portion adapted to enclose and secure around a patient's amputation stump, said flexible cylindrical portion having a diameter, an open top end, an open bottom end, an axial opening therein extending between said open top and bottom ends to define two axial opening edges, said axial opening edges including first detachable fastening means, means for adjusting said diameter of said cylindrical portion;

a semi-rigid cup portion adapted to fit upon said bottom portion of said amputation stump; and second detachable fastening means, said second detachable fastening means co-axially and detachably connecting said cup portion to said bottom end of said cylindrical portion.

2. A removable flexible dressing as claimed in claim 1 wherein said cup portion comprises a circular bottom having a periphery and a cylindrical wall, said cylindrical wall extending upwardly from said periphery of said circular bottom.

3. A removable flexible dressing as claimed in claim 1 wherein one of said axial opening edges overlaps the other axial opening edge.

4. A removable flexible dressing as claimed in claim 1 wherein said detachable fastening means comprises self gripping fastener means.

5. A removable flexible dressing as claimed in claim 1 and further comprising a gripping fastener means.

6. A removable flexible dressing as claimed in claim 1 and further comprising a belt of non-slip fabric spaced above said cylindrical portional and encircling a leg amputation stump above the knee, said flexible cylindrical portion being disposed below the knee, and at least two oppositely disposed straps interconnecting said belt and said cylindrical portion.

* * * * *